United States Patent [19]

Cortes et al.

[11] Patent Number: 5,240,604
[45] Date of Patent: Aug. 31, 1993

[54] MULTIDIMENSIONAL CHROMATOGRAPHIC SYSTEM

[75] Inventors: Hernan J. Cortes; Curtis D. Pfeiffer; Steven J. Martin; Charles G. Smith; Gary L. Jewett, all of Midland, Mich.

[73] Assignee: The Dow Chemical Company, Midland, Mich.

[21] Appl. No.: 982,265

[22] Filed: Nov. 25, 1992

Related U.S. Application Data

[63] Continuation of Ser. No. 561,359, Jul. 31, 1990, abandoned, which is a continuation of Ser. No. 243,913, Sep. 13, 1988, abandoned.

[51] Int. Cl.$^5$ ............................................ B01D 15/08
[52] U.S. Cl. ............................... 210/198.2; 210/656; 210/659; 422/70; 422/78; 422/80; 422/89; 96/101
[58] Field of Search ............ 210/635, 656, 659, 198.2; 55/197, 386; 422/70, 78, 80, 89; 436/155, 161

[56] References Cited

U.S. PATENT DOCUMENTS

| | | | |
|---|---|---|---|
| 2,610,107 | 9/1952 | Dreher | 422/78 |
| 3,518,059 | 6/1970 | Levy | 422/78 |
| 3,572,092 | 3/1971 | Zernow | 422/78 |
| 4,087,249 | 5/1978 | Okumoto | 422/78 |
| 4,159,894 | 7/1979 | Hu | 422/78 |
| 4,234,315 | 11/1980 | Scott | 422/78 |
| 4,325,907 | 4/1982 | Dembicki | 422/89 |
| 4,344,917 | 5/1982 | Schorno | 422/78 |
| 4,391,776 | 7/1983 | Braun | 422/78 |
| 4,484,061 | 11/1984 | Zelinka | 210/198.2 |
| 4,726,822 | 2/1988 | Cates | 210/198.2 |
| 4,935,145 | 6/1990 | Cortes et al. | 210/656 |

FOREIGN PATENT DOCUMENTS

| | | | |
|---|---|---|---|
| 0073176 | 2/1983 | European Pat. Off. | 210/656 |
| WO8303676 | 10/1983 | PCT Int'l Appl. | 210/656 |
| 711466 | 5/1990 | U.S.S.R. | 210/656 |
| 916316 | 1/1963 | United Kingdom | 210/656 |
| 1227260 | 4/1971 | United Kingdom | 210/656 |

OTHER PUBLICATIONS

"On-line Multidimensional Chromatography Using Micro HPLC and Capillary GC", by H. J. Cortes and C. D. Pfeiffer, Chromatography Forum, 4 (1986) pp. 29–34.

"Determination of Trace Chlorinated Benzenes in Fuel Oil by On-line Multidimensional Chromatography Using Packed-Capillary Liquid Chromatography and Capillary Gas Chromatography", H. J. Cortes, B. E. Richter, C. D. Pfeiffer and D. E. Jensen, J. Chromatography, 349 (1985) pp. 55–61.

"On-Line Multidimensional Chromatography Using Packed Capillary Liquid Chromatography and Capillary Gas Chromatography", H. J. Cortes, C. D. Pfeiffer, and B. E. Richter, J. High Resolution Chromatography and Chromatography Communications, 8 (1985) pp. 469–474.

"Coupling Micro-LC and Capillary GC as a Powerful Tool for the Analysis of Complex Mixtures", D. Duguet, C. Dewaele and M. Verzele, 11 J. High Resolution Chromatography and Chromatography Communications, 11 (1988) pp. 252–256.

"Fused Silica Narrow Bore Microparticle Packed Column HPLC", F. J. Yang, J. Chromatography 236 (1982) p. 265.

"Analysis of Compositional and Structural Heterogene- (List continued on next page.)

Primary Examiner—Ernest G. Therkorn

[57] ABSTRACT

An on-line multidimensional system which includes a liquid chromatograph having an on-line connection to a pyrolysis probe, which in turn has on-line connection to a gas chromatograph. Preferred applications use a size-exclusion chromatograph coupled to a pyrolysis probe coupled to a gas chromatograph to simultaneously produce composition as a function of molecular weight/size information for polymeric materials.

19 Claims, 4 Drawing Sheets

OTHER PUBLICATIONS ities of Polymers by Non-Exclusion HPLC", G. Glockner, Advances in Polymer Science, 79 (1986) pp. 159-214.

Journal Article by T. V. Raglione and R. A. Hartwick, J. Chromatography, 454 (1988) 157-167.

"Direct Introduction of Aqueous Eluents for On-Line Coupled Liquid Chromatography-Capillary Gas Chromatography", by H. J. Cortes, C. D. Pfeiffer G. L. Jewett, and B. E. Richter, J. Microcolumn Separations, vol. 1, No. 1 (1989) pp. 28-34.

Introduction to Modern Liquid Chromatography by J. Kirkland & L. Snyder pp. 218-219 and 222-223, John Wiley & Sons, 1979, New York.

Handbook of Derivatives for Chromatography by K. Blan and G. King pp. 1-4 Heyden & Sons, Ltd., London 1978.

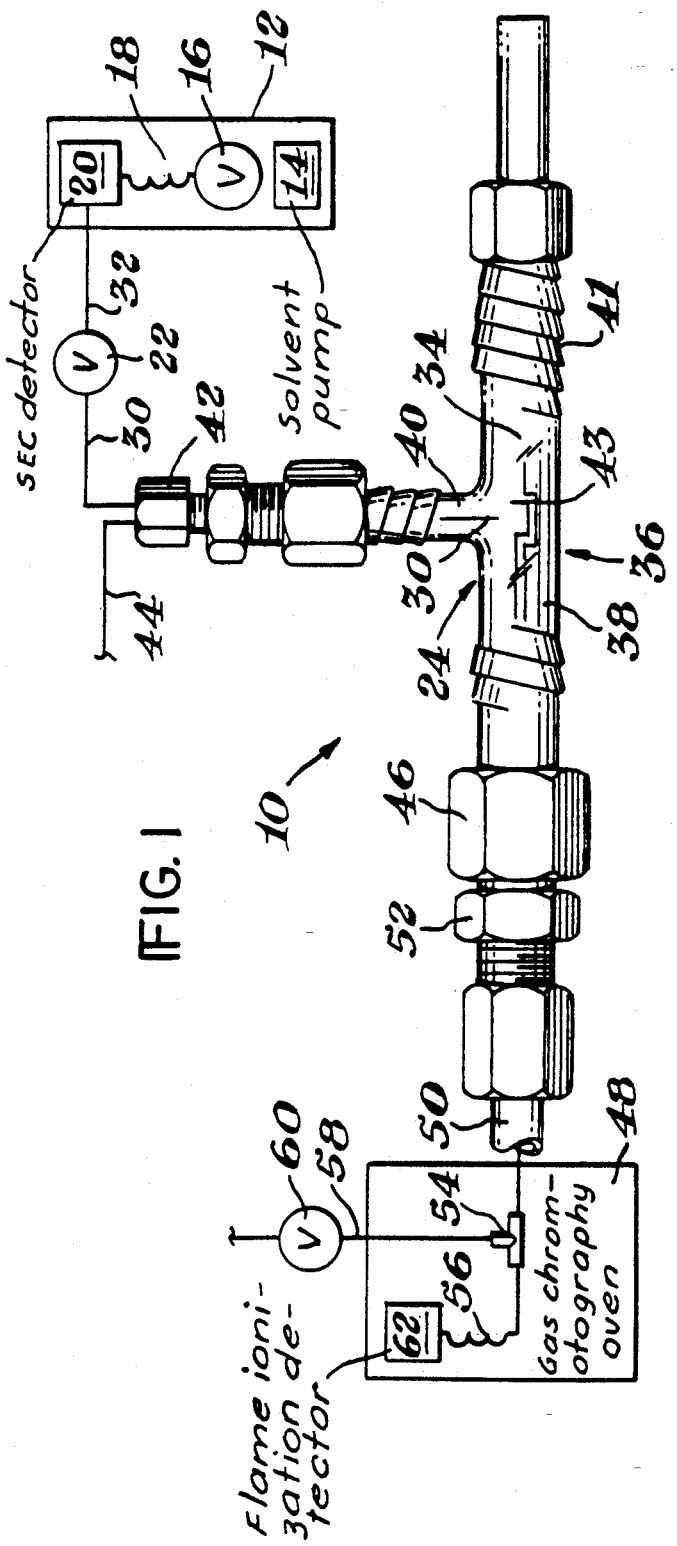
FIG. 1
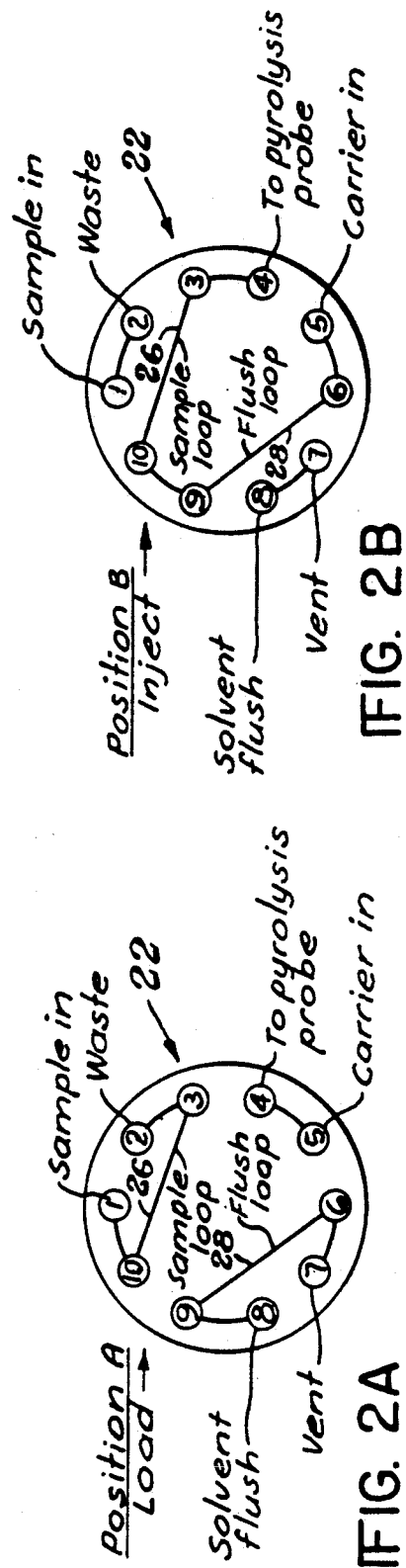
FIG. 2A
FIG. 2B

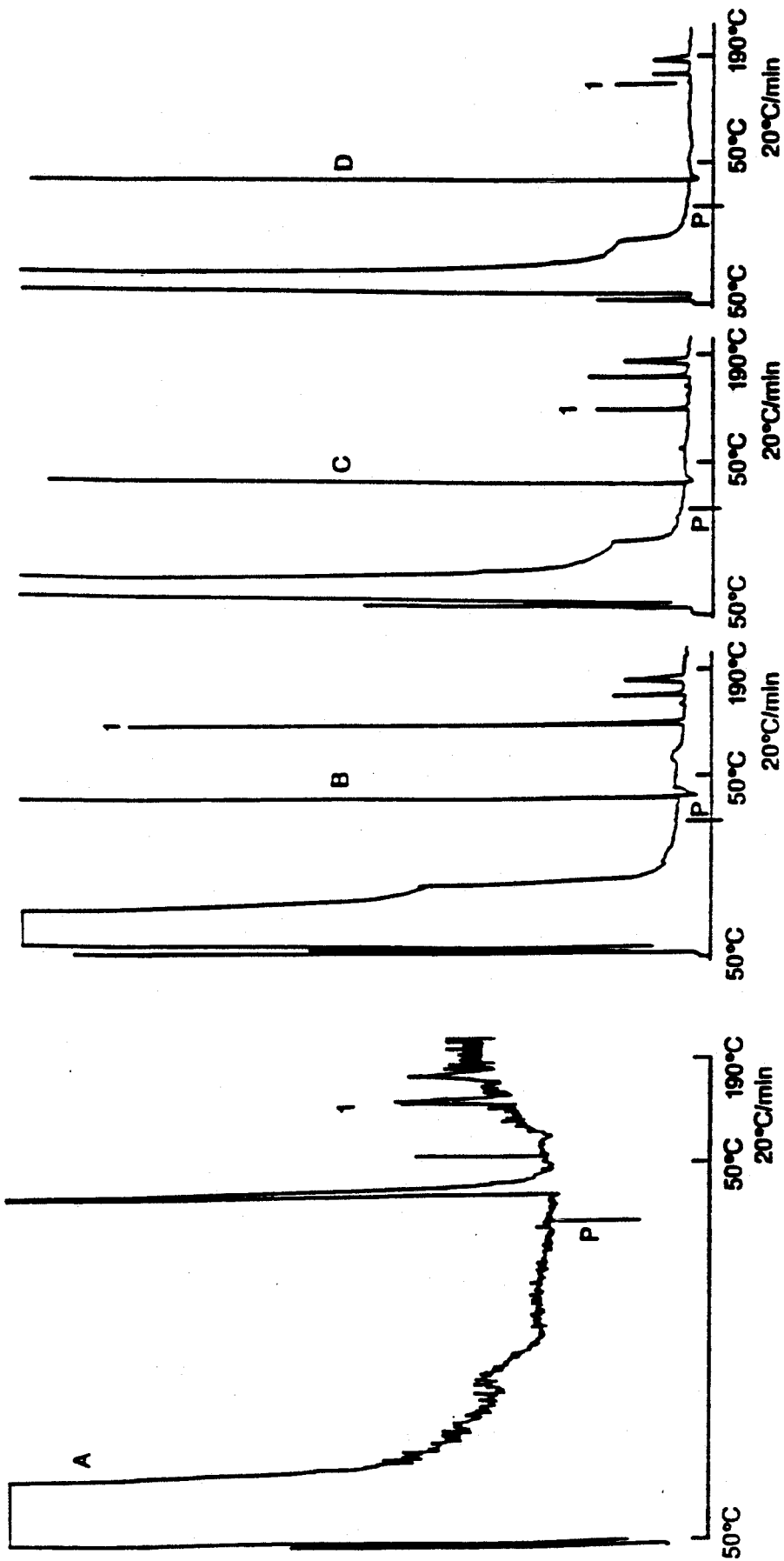

MULTIDIMENSIONAL CHROMATOGRAPHIC SYSTEM

CROSS-REFERENCE TO RELATED APPLICATION

This is a continuation of application Ser. No. 07/561,359, now abandoned, which, in turn, is a continuation of application Ser. No. 243,913, filed Sep. 13, 1988, now abandoned.

BACKGROUND AND SUMMARY OF THE INVENTION

The present invention generally relates to multidimensional chromatography, and particularly to an on-line coupled LC/GC system which is capable of generating information for compounds containing nonvolatile components.

Multidimensional chromatography can be a powerful separation tool, especially when dealing with complex matrices which may require unattainably high theoretical plate counts for adequate resolution. Similarly, multidimensional chromatography has been found quite useful when dealing with samples that require tedious clean-up steps prior to analysis. The combination of a liquid chromatograph (LC) and a gas chromatograph (GC) in an "on-line" mode has been described in the following references: "On-Line Multidimensional Chromatography Using Packed Capillary Liquid Chromatography And Capillary Gas Chromatography", by H. J. Cortes, C. D. Pfeiffer, B. E. Richter, in HRC & CC, 8 (1985) 469., "Determination Of Trace Chlorinated Benzenes In Fuel Oil By On-Line Multidimensional Chromatography Using packed Capillary Liquid Chromatography And Capillary Gas Chromatography", by H. J. Cortes, C. D. Pfeiffer, B. E. Richter, D. E. Jensen, in J. Chromatogr., 349 (1985) 55; and "On-Line Multidimensional Chromatography Using Micro HPLC-Capillary GC", by H. J. Cortes, C. D. Pfeiffer, in Chromatography Forum, 4 (1986) 29. These articles are incorporated herein by reference.

As discussed in these articles, columns for High Performance Liquid Chromatography (HPLC) have been used in an on-line mode primarily for the determination of trace components in complex matrices, where the LC provides a highly efficient clean-up step, and a section of the chromatogram containing the components of interest is transferred to a GC for further resolution and quantification. A similar system has also been used to separate components by class, as discussed in "Coupling Micro LC-Capillary GC As A Powerful Tool For The Analysis Of Complex Mixtures", by D. Duquet, C. Dewaele, M. Verzele, in HRC & CC, 11 (1988) 252.

Nevertheless, a principal limitation to the use of this LC/GC technology is the type of compounds that can be analyzed by the GC. In other words, the compounds must be volatile and chromatographable in the gas phase. Nonvolatile or highly polar compounds can be analyzed by a GC if they are chemically treated (derivatized) to convert them into a more suitable form. In this regard, see the "Handbook of Derivatives For Chromatography", by K. Blau, and G. King, Heyden & Son, Ltd., London (1978). However, the need to chemically treat these compounds makes it very difficult to provide an on-line or uninterrupted multidimensional analysis of such nonvolatile or highly polar compounds.

Another alternative is the use of pyrolysis gas chromatography to examine the volatile pyrolysis fragments of a nonvolatile molecule. In the characterization of polymers, the combination of size-exclusion chromatography (SEC) and pyrolysis gas chromatography will enable the determination of average polymer composition as a function of molecular size/weight. However, this type of information is difficult to obtain, since fractions eluting from an SEC system are usually collected manually, evaporated, redissolved in an appropriate solvent and manually transferred to a pyrolysis probe via a syringe.

Accordingly, it is a principal objective of the present invention to provide a system for coupling liquid and gas chromatography which will permit on-line multidimensional analysis or determinations of nonvolatile or highly polar compounds. In this regard, the term "nonvolatile" will be used herein to refer to compounds having nonvolatile and/or highly polar characteristics.

It is another objective of the present invention to combine size-exclusion chromatography (SEC) and pyrolysis gas chromatography in an on-line system to permit the determination of the average polymer composition as a function of molecular size/weight, as well as to provide valuable information which can be used to understand polymer properties and polymerization chemistry.

It is a further objective of the present invention to provide an on-line multidimensional system which is capable of automatically collecting fractions of interest from an SEC and transferring them to an interface for permitting GC analysis.

To achieve the foregoing objectives, the present invention provides an on-line multidimensional system which includes a micro size-exclusion chromatograph, and a switching valve for sampling fractions eluting from the SEC. The switching valve directly transfers these sampled fractions to a pyrolysis probe, which produces volatile fragments representative of the nonvolatile components from the sampled fractions. The system also includes a gas chromatograph for providing molecular size/weight distribution information from the volatile fragments. The present invention also enables the combination of the valve, pyrolysis probe and gas chromatograph to be used as an autoinjector when the SEC or other LC is not connected to the system.

The switching valve combines separate sample and solvent flush loops, and causes a carrier fluid to sequentially convey the contents of these loops to the pyrolysis probe. The pyrolysis probe includes a pyrolysis ribbon which is coaxially disposed within a glass housing. The housing for the pyrolysis probe includes a lateral well portion which directs the sampled fractions to a confined area of the pyrolysis ribbon. The pyrolysis probe housing also permits the introduction of an auxiliary carrier fluid to increase the solvent evaporation rate and minimize the opportunity for the solvent to spread along the pyrolysis ribbon.

Additional advantages and features of the present invention will become apparent from a reading of the detailed description of the preferred embodiments which makes reference to the following set of drawings in which:

BRIEF DESCRIPTION OF THE DRAWINGS

FIG. 1 is a diagrammatic view of an on-line multidimensional system according to the present invention.

FIGS. 2A and 2B are diagrammatic views of the load and injection positions of the multi-port switching valve shown in FIG. 1.

FIGS. 5A-5D are graphs which represent capillary GC chromatograms obtained from a polystyrene homopolymer at varying split ratios.

DETAILED DESCRIPTION OF THE PREFERRED EMBODIMENT

Figure 3:
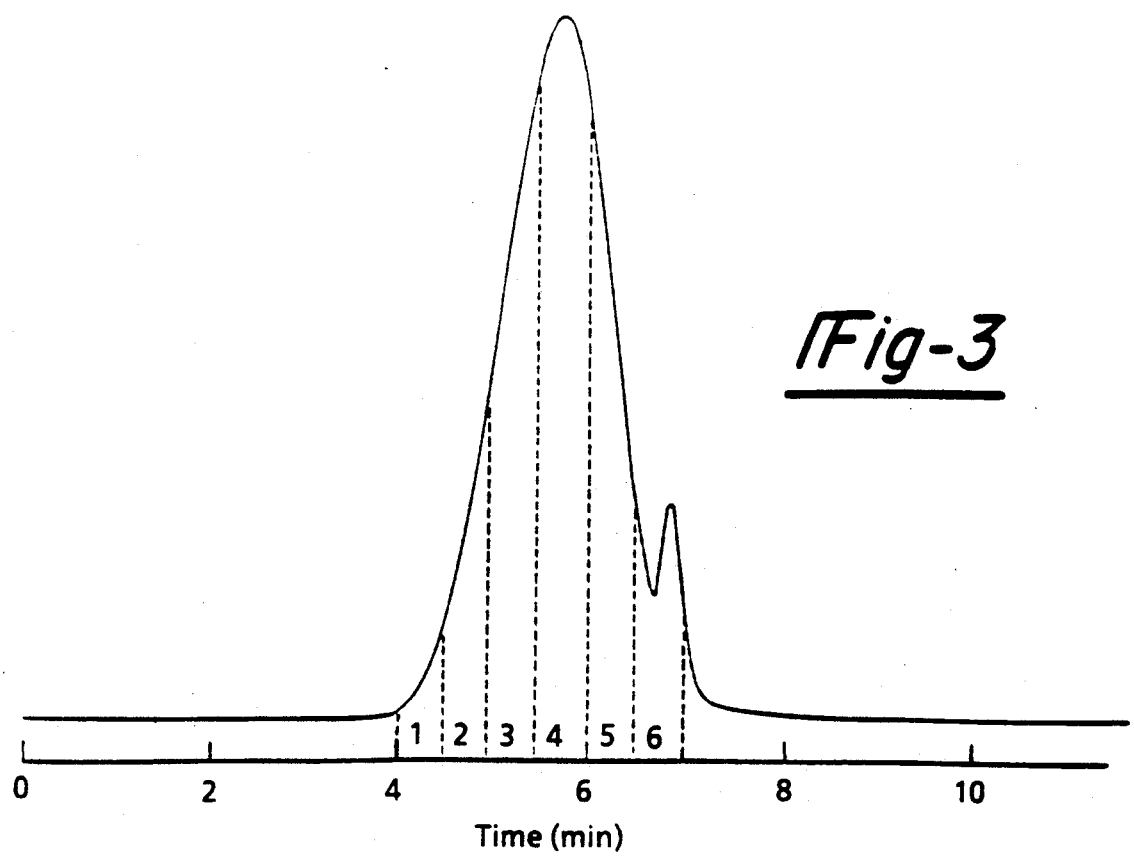
FIG. 3 is a graph which represents a micro SEC chromatogram of a styrene-actrylonitrile copolymer.

Referring to FIG. 1, an on-line multi-dimensional chromatographic system 10 according to the present invention is shown. The system 10 includes a liquid chromatograph 12, which has a solvent Pump 14, an injection valve 16, one or more columns 18 and a detector 20. In one embodiment according to the present invention, the solvent pump is an Isco $\mu$-LC 500 solvent delivery system (Isco, Lincoln, Nebr., USA), operated at a constant flow rate. Similarly, the injection valve 16 is a Valco model NI4W injection valve (Valco Instruments, Houston Tex., USA), with an injection volume of 200 nl. Additionally, the detector 20 is a Jasco Uvidec V detector (Jasco International, Japan), which is equipped with a modified cell whose illuminated volume was calculated to be 6 nl from the capillary diameter and slit size. A discussion of such a modified cell may be found in "Fused Silica Narrow Bore Microparticle Packed Column HPLC", by F. J. Yang, in J. Chromatogr. 236 (1982) 265. This article is hereby incorporated by reference.

The columns 18 were constructed of fused silica capillaries with an internal diameter of 250 $\mu$m, (Polymicro Technologies, Phoenix, Ariz., USA), with a column length of 50 cm. A porous ceramic bed support was used, as discussed in "Porous Ceramic Bed Supports For Fused Silica Capillary Columns Used In Liquid Chromatography", by H. J. Cortes, C. D. Pfeiffer, B. R. Richter, and T. S. Stevens, in HRC & CC, 10 (1987) 446. This article is hereby incorporated by reference. The columns 18 were packed with Zorbax PSM-1000 of 7-$\mu$m particle diameter, as a slurry in acetonitrile (5:1), at 6000 psig.

The liquid chromatograph 12 is preferably a micro SEC system, (e.g., for the characterization of polymers). However, there is no intent to limit the invention in its broad aspects to a micro system or size exclusion chromatography since the selection of the column dimension and type will be determined by the sample and information desired. In this regard, a micro SEC system was chosen for the LC 12, because the components of interest are diluted in much less volume when compared to a conventional SEC column. This feature allows the investigation of a polymer in relatively few analyses. However, if a more detailed examination is desired, smaller cuts or fractions can be analyzed. Alternatively, microbore or conventional columns could be used. Therefore, the analysis can provide a larger number of determinations over a narrower molecular size interval. Since an SEC separates molecules based on size, and the size of a molecule is related to its molecular weight, the term "molecular size/weight" is used herein to generically refer to molecular size and/or molecular weight.

The system 10 also includes a multi-port switching valve 22 for transferring the fractions of interest eluting from the micro SEC 12 to a pyrolysis probe 24. In one embodiment of the present invention, the valve 22 is a Valco ten port valve model NI10WT. As shown in FIGS. 2A and 2B this valve was equipped with a 1.0 $\mu$l sample loop 26 and a 5.0 $\mu$l solvent flush loop 28. Both of these loops 26-28 were made from 50 $\mu$m I.D. silica tubing. A short length of this tubing was also used for the conduit 30 which connects the valve 22 to the pyrolysis probe 24, as well as the conduit 32 which connects the valve 22 to the detector 20 of the micro SEC 12.

FIG. 2A shows the valve 22 in a "load" position, which creates the separate sample and flush loops. In contrast, FIG. 2B shows the valve 22 in an "inject" position, which combines the sample and flush loops. In the load position, the effluent from the SEC detector 20 flows through the sample loop 26 via the conduit 32. Output flow from the sample loop 26 may be stored or transferred to a waste receptacle. Similarly, with the valve 22 in the load position, a suitable solvent (e.g. THF) will flow through and out of the flush loop 28.

When the valve 22 is switched to the inject position, the sample loop 26 will be combined with the flush loop 28, so that the contents of these loops will be conveyed to the pyrolysis probe 24 by a suitable carrier fluid (e.g., Helium). In addition, another gas such as air can be introduced to allow cleaning of the system. While other suitable switching valve arrangements may be used in the appropriate application, the use of a flush loop is preferred because it permits the transfer lines from the micro SEC 12 to the pyrolysis probe 24 to be cleared before the next sample is collected.

While the preferred valving arrangement is one which first traps a predetermined quantity of the effluent from the SEC 12 in a sample loop, other suitable valving arrangements may be employed in the appropriate application. For example, a valve structure could be employed which chooses between an inject mode and a bypass mode, such that the effluent flow will be passed to the pyrolysis probe, unless the flow is diverted or bypassed to a waste receptacle. Once the effluent flow is diverted, then a carrier fluid may be used to convey the effluent passed through the valve to the pyrolysis probe 24.

The pyrolysis probe 24 is generally comprised of a pyrolysis ribbon 34 which is coaxially disposed in a glass chamber or housing 36. In one form of the present invention, the pyrolysis unit used is a Hewlett Packard Model 18580A pyroprobe (Hewlett Packard Instruments, Avondale Pa., USA), which was operated at 700° C. for one second intervals. The housing 36 includes a cylindrical portion 38 through which the pyrolysis ribbon 34 extends, and a lateral cylindrical portion 40 which extends from the cylindrical portion in a generally perpendicular direction. The housing 36 is also wrapped with a heating tape 41, which is heated at the appropriate time to approximately 180° C. (outside surface temperature).

In accordance with one aspect of the present invention, a depression or well portion 43 is formed in the pyrolysis ribbon 34 directly beneath the lateral portion 40 of the housing 36. The well portion 43 in the pyrolysis ribbon 34 is used to receive the individually sampled fractions of interest from the valve 22 via conduit 30. In this regard, the well 43 serves to confine this fluid flow in a specified area of the pyrolysis ribbon 34. Accordingly, the well 43 will cause the transferred fraction to be deposited onto a confined, reproducible area of the pyrolysis ribbon 34.

The inlet port 42 of the lateral portion 40 also permits an auxiliary carrier gas (e.g., helium, nitrogen or air) to enter the housing 36 via conduit 44. The flow rate of this auxiliary carrier gas may be adjusted to control the evaporation rate of the solvent transferred into the pyrolysis probe 24. This feature enables the evaporation rate to be increased, thereby minimizing the opportunity for the solvent and sample to spread on the pyrolysis ribbon 34.

The housing 36 of the pyrolysis probe 24 also includes an outlet port 46, which permits the volatile fragments produced by the pyrolysis ribbon 34 to be transferred to a gas chromatograph 48. A short capillary tube 50 extends from the outlet port 46, and fittings 52 are used to connect the capillary tube to a low dead volume three way tee 54 (SGE, Melbourne, Australia). The tee 54 is used to split the output flow from the pyrolysis probe 24. One portion of this flow is directed to the columns 56 of the gas chromatograph 48, while the remaining portion is vented through conduit 58. A micro metering valve 60 is connected to the conduit 58 to control the split ratio of vented fluid to GC transferred fluid. Alternatively, a switching valve such as Valco Model N4WT can be placed between the housing outlet 50, and split tee 54, to allow rapid venting of the solvent.

In one embodiment according to the present invention, the gas chromatograph used is a Varian model 3700 gas chromatograph (Varian Associates, Walnut Creek, Calif., USA) having a flame ionization detector 62. Similarly, the analytical columns 56 were a 50 m×0.20 mm I.D. phenyl-methyl silicone of 0.33 $\mu$m film thickness (Hewlett-Packard, Avondale, Pa. USA). The temperature program used was 50° C. for 6 minutes, then to 220° C. at 10° or 20° C./min. The temperature program was initiated at the time of pyrolysis, which preferably took place after the solvent eluted from the system. The carrier gas used was Helium, and the make up gas to the detector 62 was Nitrogen (at 20 ml/min.).

Before conducting experiments with the system 10, the SEC columns 18 were evaluated and calibrated using narrow distribution anionic polystyrene standards (Polymer labs, England). Column performance was estimated by measuring the asymmetry factor, as discussed in "Introduction to Modern Liquid Chromatography", by J. Kirkland, L. Snyder, J. Wiley & Sons, NY (1979). In the case of toluene as the totally permeated molecule, the asymmetry factor was found to be 1.04, and the column efficiency was found to be 38,000 plates/meter. Resolution was estimated according to the following equation:

$$R = D\partial = [d \log M/dV(\Delta V) = d \log M,$$

where D=the slope of the calibration curve, $\partial$=the standard deviation of toluene, V=the elution volume, and M=the molecular weight. In the embodiment described, the resolution factor obtained was 0.034.

The elution volume is an SEC system is known to increase with the sample concentration due to the change in hydrodynamic volume of a polymer in solution with concentration. In addition, high sample concentrations may cause band broadening due to viscous streaming of the solute band. Accordingly, for the specific polymer and conditions, it is preferred that the amount of polymer injected into the SEC columns 18 not exceed 2 $\mu$g in order to achieve accurate molecular weight distributions, as based upon the calibration procedure discussed above.

The preferred mobile phase solvent used for this specific application, was HPLC grade tetrahydrofuran (Fisher Scientific, Fairlawn, N.J., USA). In this regard, the solvent flow rate was 2.0 $\mu$l/min., which yielded a column head pressure of 1300 psig. It is known that instrumental flow rate fluctuation can cause large errors in the calculated sample molecular weight. Accordingly, in order to compensate for any flow rate fluctuations that could be experienced, it is preferred that a small amount of Toluene be added to the polymer solution being injected in order to provide an internal standard.

Figure 4:
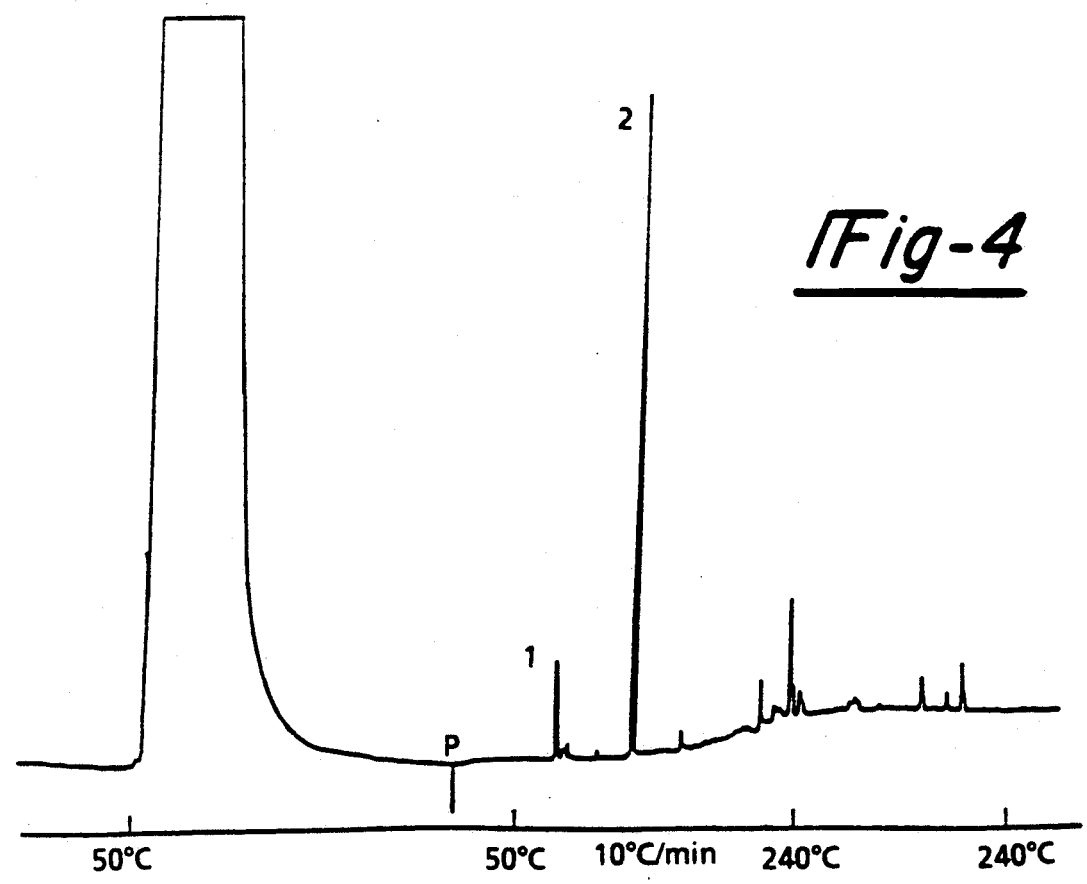
FIG. 4 is a graph which represents a capillary GC chromatogram obtained from the pyrolyzed products of a fraction of the styrene-actrylonitrile shown in FIG. 3.

The application of the on-line SEC/pyrolysis GC system 10 to the characterization of a stryene-acrylonitrile copolymer is presented in FIGS. 3 and 4. FIG. 3 represents the micro SEC chromatogram obtained on the polymer prepared by dissolving 10 mg/ml in THF. The various fractions transferred to the pyrolysis interface 24 are indicated in the chromatogram. FIG. 4 represents the capillary GC chromatogram obtained after pyrolysis on the fraction number 1 from FIG. 3 whose molecular weight was between 1,800,000 and 450,000. This GC chromatogram is considered typical of the GC chromatograms obtained after pyrolysis of the appropriate section across the molecular weight distribution.

The relative composition of copolymer eluted in each fraction was estimated by measuring the area ratios of the acrylonitrile and styrene peaks generated. This information is valuable in determining the relative composition as a function of molecular size. In this regard, it was found that the configuration of the pyrolysis probe has an effect on the variability of the area ratio data. When pyrolysis takes place, the platinum ribbon 34 flexes and seldom returns exactly to its original position. Accordingly, it is difficult to deposit the fractions of interest at the same site of the ribbon as previous fractions, due to this orientation change. Since the ribbon 34 does not heat evenly throughout its length, the transferred fractions may experience different pyrolysis temperatures, and yield variable results. However, as discussed above, the provision of the well 43 in the pyrolysis ribbon 34 confines the transferred fractions to a reproducible area, and enables an acceptable standard deviation of the area ratios to be achieved (e.g., 2.4%).

Ideally, the total fraction pyrolyzed should be transferred to the GC columns 56. However, it was found that the pyrolysis interface 24 had to be swept at a high carrier gas flow rate in order to obtain relatively sharp peaks. This situation was also complicated by the fact that the GC columns 56 generated relatively high pressures, and therefore resisted the use of high flow rates from the pyrolysis interface 24. In this regard, it should be noted that the provision of the split tee 54 was instrumental in enabling sufficiently high flow rates to be achieved. Alternatively, the use of wide-bore capillaries may allow rapid transfer of the fragmented components to the columns 56 without resorting to a split ratio system. Alternatively, the function of the split can be accomplished by replacing it with a cryogenic focusing scheme or a trap such as a solid absorbent.

Referring to FIGS. 5A–5D, a series of GC chromatograms are shown to illustrate the experimental effect of various split ratios at the tee 54 under the control of the valve 60. For these experiments, the sample was prepared by dissolving 70 mg of a polystyrene homopolymer in 10 ml of THF. A 1.0 μl aliquot of this solution was transferred to the pyrolysis interface 24 by manually filling the sample loop 26 of the switching valve 22 with a syringe for each of the split ratio experiments. Additionally, it should be noted that the columns employed were 50 m×0.2 mm I.D. 5% phenylmethyl silicone (df=0.3 μm). The GC oven temperature program used was 50° C. to 240° C. at 10 c/min. The carrier gas used was Helium at 60 cm/sec., and the makeup carrier gas used was Nitrogen at 20 ml/min. The GC detector 62 was set for FID at 320° C., and a split ratio between the columns 56 and the detector 62 was varied.

FIG. 5A represents an analysis without any split being employed at the tee 54 (i.e., the total aliquot was transferred to the columns 56 of the gas chromatograph 48). As shown in FIG. 5A, the analysis yielded a high background noise level, an overlong solvent peak, and the peak of interest (in this case styrene) was broad and split at the top. However, as shown in FIG. 5B, a split ratio of 10:1 resulted in much improved chromatography. In this respect, it should be understood that the needle valve 60 was opened such that 10 parts of the fluid flow from the pyrolysis interface 24 would be vented part transferred to the GC columns 56. As for FIG. 5C, the split ratio used was 20:1. Similarly, the split ratio used to obtain the chromatogram shown in FIG. 5D was 30:1. From these two figures, it should be appreciated that the chromatography was not materially affected, except that the sensitivity was decreased. Accordingly, a split ratio of 10:1 is preferably employed for this particular application of multi-dimensional analysis according to the present invention.

Figure 6B:
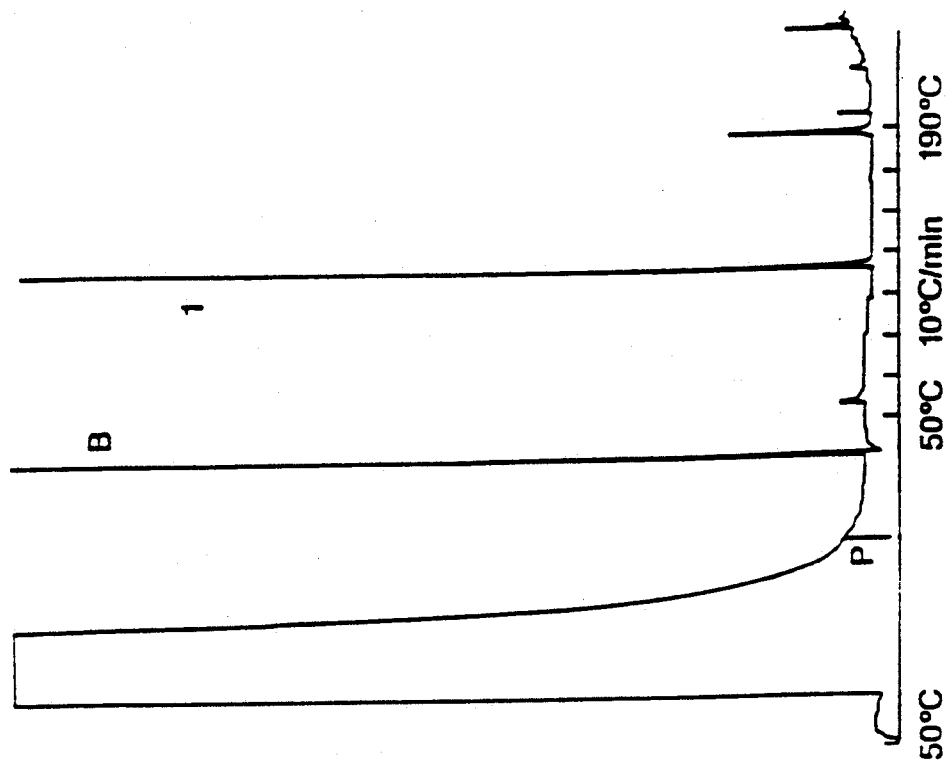
FIGS. 6A-6B are graphs which represent capillary GC chromatograms obtained from a styrene homopolymer at two different interface temperatures.
Figure 6A:
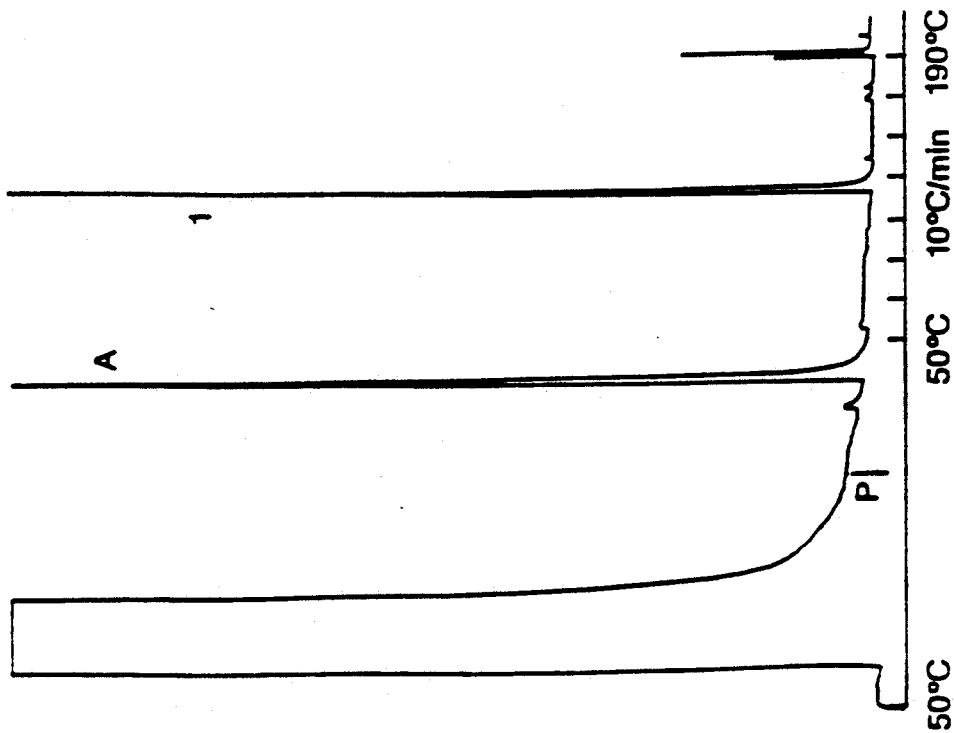

The temperature of the pyrolysis interface 24 will also have an affect on the chromatography. For example, in classical Pyrolysis GC, the interface is heated to minimize condensation of the fragments of interest and avoid poor chromatography. With respect to the multidimensional system 10 according to the present invention, FIGS. 6A and 6B show the effect of two different pyrolysis interface temperatures. Both of these GC chromatograms were obtained by chromatographing the pyrolysis products of a styrene homopolymer, which was prepared and deposited onto the pyrolysis ribbon 34 in accordance with the procedure set forth above for investigating the effect of various split ratios.

FIG. 6A represents the chromatogram obtained at an interface temperature of 25° C., while FIG. 6B represents the results obtained at an interface temperature of 180° C. As shown in these figures, the peak shapes improved considerably at the higher interface temperature. However, it was found that when the transfer was made while the interface 24 was heated, the sample tended to splatter and deposit some of the polymer on the interface walls rather than on the pyrolysis ribbon 34. This yielded reduced sensitivity and made the reproducibility of the results unpredictable. Accordingly, it is preferred that the transfer of the fractions of interest be made at a temperature which does not create excessive boiling, dependant upon the solvent used. Once the transfer is completed, the interface 24 may then be heated to an appropriate temperature, such as 180° C.

It will be appreciated that the above disclosed embodiment is well calculated to achieve the aforementioned objects of the present invention. In addition, it is evident that those skilled in the art, once given the benefit of the foregoing disclosure, may now make modifications of the specific embodiment described herein without departing from the spirit of the present invention. Such modifications are to be considered within the scope of the present invention which is limited solely by the scope and spirit of the appended claims.

What is claimed is:

1. A chromatographic apparatus for providing on-line multidimensional analysis of a sample containing a nonvolatile component comprising:
    liquid chromatographic means for separating a sample having a nonvolatile component into a fraction of interest comprising said nonvolatile component;
    pyrolysis means;
    automatic means for collecting and transferring a fraction of interest eluting from the liquid chromatographic means to the pyrolysis means;
    gas chromatographic means arranged for receiving and separating into components at least a portion of the gas effluent of the pyrolysis means; and
    means for detecting said fraction of interest after passing through said gas chromatographic means to permit the generation of information on said nonvolatile components.

2. The on-line chromatographic system according to claim 1, wherein said liquid chromatographic means is a size-exclusion chromatograph.

3. The on-line chromatographic system according to claim 2, wherein the size-exclusion chromatographic is a micro size-exclusion chromatograph.

4. The on-line chromatographic system according to claim 3, wherein said transfer means includes valve means for selectively sampling a predetermined volume of said fractions eluting from said micro size-exclusion chromatograph and transferring said sampled fractions to said pyrolysis means.

5. The on-line chromatographic system according to claim 4, wherein said valve is a switching valve having an inject mode and a bypass mode allowing direct transfer of the liquid chromatographic effluent to the pyrolysis means.

6. The on-line chromatographic system according to claim 3, wherein said valve means is a multi-port switching valve having a load position and an injection position, said load position providing separate sample and flush loops, and said injection position combining said sample and flush loops and causing a carrier fluid to sequentially convey the contents of said sample and flush loops to said pyrolysis means.

7. The on-line chromatographic system according to claim 1, wherein said pyrolysis means includes a pyrolysis ribbon contained in a housing having inlet means for receiving said sampled fractions from said liquid chromatographic means and causing said sample fractions to contact said pyrolysis ribbon, and outlet means for transferring said produced fragments to said gas chromatographic means.

8. The on-line chromatographic system according to claim 7, wherein said pyrolysis ribbon has a depression to confine the transferred section to a reproducible area.

9. The apparatus of claim 8, wherein said pyrolysis ribbon is coaxially disposed within the axis of said housing, and said depression for said pyrolysis is positioned below a lateral portion of said housing which receives sampled fractions from said valve means.

10. The apparatus of claim 9, wherein said pyrolysis means includes a means for heating said housing.

11. The apparatus of claim 10, wherein said means for heating is a heating tape which is wrapped around said housing.

12. The on-line chromatographic system according to claim 7, wherein said inlet means of said housing also includes a port for receiving an auxiliary carrier fluid.

13. The on-line chromatographic system according to claim 1, wherein said gas chromatographic means includes splitter means for causing one portion of the gas effluent from said pyrolysis means to be vented while causing the remaining portion of the gas effluent to be transferred to a column of said gas chromatographic means.

14. A chromatographic apparatus for providing on-line multi-dimensional analysis of compounds containing nonvolatile components, comprising:
   a size-exclusion chromatograph;
   valve means for sampling fractions eluting from said size-exclusion chromatograph, said valve means connects a carrier fluid source which causes said sampled fractions to be conveyed from said valve means;
   a pyrolysis means in communication with said valve means for producing volatile fragments which are representative of said nonvolatile components from said sampled fractions;
   splitter means for receiving gas effluent from said pyrolysis means while venting a portion of said gas effluent, and transferring a portion of said gas to gas chromatograph means; and
   gas chromatograph means for receiving a portion of said fragments from said pyrolysis means by way of said splitter means for analysis of said volatile fragments; and
   means for detecting said fragments after passing through said gas chromatographic means to permit the generation of information on said nonvolatile components.

15. The apparatus of claim 14, wherein said pyrolysis means includes a pyrolysis ribbon contained in a housing having inlet means for receiving said sampled fractions from said size-exclusion chromatographic means, and an outlet means for transferring said produced fragments to said gas chromatographic means.

16. The apparatus of claim 15, wherein said pyrolysis ribbon is provided with a depression to confine said sampled fractions to a reproducible area.

17. The apparatus of claim 15, wherein said pyrolysis ribbon is coaxially disposed within said housing, and said depression for said pyrolysis is positioned below a lateral portion of said housing which receives sampled fractions from said valve means.

18. The apparatus of claim 17, wherein said pyrolysis means includes a means for heating said housing.

19. The apparatus of claim 18, wherein said means for heating is a heating tape which is wrapped around said housing.

* * * * *

UNITED STATES PATENT AND TRADEMARK OFFICE
CERTIFICATE OF CORRECTION

PATENT NO. : 5,240,604
DATED : August 31, 1993
INVENTOR(S) : Hernan J. Cortes, et. al.

It is certified that error appears in the above-indentified patent and that said Letters Patent is hereby corrected as shown below:

Column 8, Claim 7, Line 57, "chromatographic means and causing said sample fractions to" should correctly read--chromatographic means and causing said sampled fractions to --.

Signed and Sealed this

Seventeenth Day of May, 1994

Attest:

BRUCE LEHMAN

Attesting Officer

Commissioner of Patents and Trademarks